(12) United States Patent
Sathyanarayana

(10) Patent No.: US 7,578,790 B2
(45) Date of Patent: Aug. 25, 2009

(54) SYSTEMS AND METHODS FOR DETECTING AND PRESENTING TEXTURAL INFORMATION FROM MEDICAL IMAGES

(75) Inventor: Shashidhar Sathyanarayana, Union City, CA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 450 days.

(21) Appl. No.: 10/896,104

(22) Filed: Jul. 20, 2004

(65) Prior Publication Data

US 2006/0036146 A1 Feb. 16, 2006

(51) Int. Cl.
*A61B 8/00* (2006.01)
*A61B 8/14* (2006.01)

(52) U.S. Cl. ...................... 600/443; 600/463
(58) Field of Classification Search ............ 600/458, 600/437, 462, 463, 466, 467
See application file for complete search history.

(56) References Cited

U.S. PATENT DOCUMENTS

| | | | |
|---|---|---|---|
| 4,320,765 A | 3/1982 | Cathignol et al. | |
| 4,697,594 A | 10/1987 | Mayo, Jr. | |
| 4,789,831 A | 12/1988 | Mayo, Jr. | |
| 4,805,622 A | 2/1989 | Riedlinger et al. | |
| 4,818,938 A * | 4/1989 | Sattin et al. | 324/309 |
| 4,922,917 A | 5/1990 | Dory | |
| 5,150,714 A * | 9/1992 | Green | 600/442 |
| 5,158,088 A * | 10/1992 | Nelson et al. | 600/461 |
| 5,235,984 A | 8/1993 | D'Sa | |
| 5,285,788 A | 2/1994 | Arenson et al. | |
| 5,331,964 A | 7/1994 | Trahey et al. | |
| 5,368,035 A | 11/1994 | Hamm et al. | |
| 5,469,852 A | 11/1995 | Nakamura et al. | |
| 5,486,763 A | 1/1996 | Alfano et al. | |
| 5,533,510 A | 7/1996 | Koch, III et al. | |
| 5,575,288 A | 11/1996 | Sliwa, Jr. et al. | |
| 5,615,680 A | 4/1997 | Sano | |
| 5,622,172 A | 4/1997 | Li et al. | |
| 5,669,385 A | 9/1997 | Pesque et al. | |

(Continued)

FOREIGN PATENT DOCUMENTS

GB 2210533 A 6/1989

(Continued)

OTHER PUBLICATIONS

Official Communication, U.S. Appl. No. 10/896,142 Mail date Oct. 28, 2008.

(Continued)

*Primary Examiner*—Eric F Winakur
*Assistant Examiner*—Michael T Rozanski
(74) *Attorney, Agent, or Firm*—Darby & Darby P.C.; Patrick R. Turner

(57) ABSTRACT

The invention is directed to systems and methods for detecting and presenting textural information from medical images. In one embodiment, a medical imaging system includes an imaging transducer assembly configured to emit one or more energy pulses and receive one or more echo signals, and a console, coupled to the imaging transducer assembly, configured to receive the one or more echo signals, generate an uncompressed image based on the one or more echo signals, generate a log compressed image based on the uncompressed image, generate a color overlay based on the uncompressed image, and apply the color overlay to the log compressed image.

17 Claims, 4 Drawing Sheets

U.S. PATENT DOCUMENTS

| | | | |
|---|---|---|---|
| 5,743,266 A | 4/1998 | Levene et al. | |
| 5,797,849 A | 8/1998 | Vesely et al. | |
| 5,841,889 A | 11/1998 | Seyed-Bolorforosh | |
| 5,910,115 A | 6/1999 | Rigby | |
| 5,971,923 A * | 10/1999 | Finger | 600/437 |
| 5,993,392 A * | 11/1999 | Roundhill et al. | 600/447 |
| 6,004,270 A | 12/1999 | Urbano et al. | |
| 6,042,556 A | 3/2000 | Beach et al. | |
| 6,067,371 A | 5/2000 | Gouge et al. | |
| 6,095,977 A | 8/2000 | Hall et al. | |
| 6,106,469 A * | 8/2000 | Suzuki et al. | 600/443 |
| 6,117,082 A | 9/2000 | Bradley et al. | |
| 6,152,878 A * | 11/2000 | Nachtomy et al. | 600/467 |
| 6,154,560 A | 11/2000 | Cothren et al. | |
| 6,200,267 B1 | 3/2001 | Burke | |
| 6,213,947 B1 | 4/2001 | Phillips | |
| 6,241,674 B1 | 6/2001 | Phillips et al. | |
| 6,251,074 B1 | 6/2001 | Averkiou et al. | |
| 6,306,092 B1 * | 10/2001 | Yamrom et al. | 600/447 |
| 6,364,835 B1 | 4/2002 | Hossack et al. | |
| 6,364,841 B1 * | 4/2002 | White et al. | 600/466 |
| 6,466,687 B1 | 10/2002 | Uppaluri et al. | |
| 6,512,854 B1 * | 1/2003 | Mucci et al. | 382/275 |
| 6,514,209 B1 | 2/2003 | Basude et al. | |
| 6,547,736 B1 * | 4/2003 | Moehring et al. | 600/454 |
| 6,558,326 B2 | 5/2003 | Pelissier | |
| 6,602,195 B1 | 8/2003 | Krishnan et al. | |
| 6,695,778 B2 | 2/2004 | Golland et al. | |
| 6,719,174 B1 | 4/2004 | Swift | |
| 6,719,693 B2 | 4/2004 | Richard | |
| 7,204,807 B2 | 4/2007 | Tsoref | |
| 7,215,338 B2 | 5/2007 | Horn et al. | |
| 2003/0035584 A1 | 2/2003 | Nicolas et al. | |
| 2003/0073903 A1 | 4/2003 | Sato | |
| 2003/0229287 A1 | 12/2003 | Flesch et al. | |
| 2003/0236460 A1 | 12/2003 | Ma et al. | |
| 2004/0039282 A1 | 2/2004 | Szabo et al. | |
| 2004/0059219 A1 | 3/2004 | Asafusa | |
| 2004/0193048 A1 | 9/2004 | Tsoref | |
| 2005/0149360 A1 | 7/2005 | Galperin | |
| 2006/0036146 A1 | 2/2006 | Sathyanarayana | |
| 2006/0036147 A1 * | 2/2006 | Sathyanarayana | 600/407 |
| 2006/0173318 A1 | 8/2006 | Sathyanarayan | |
| 2007/0159483 A1 | 7/2007 | Horn et al. | |

FOREIGN PATENT DOCUMENTS

WO    WO-2006019705    2/2006

OTHER PUBLICATIONS

Official Communication, U.S. Appl. No. 10/896,142 Mail date Sep. 19, 2007.

* cited by examiner

SYSTEMS AND METHODS FOR DETECTING AND PRESENTING TEXTURAL INFORMATION FROM MEDICAL IMAGES

FIELD OF THE INVENTION

The field of the invention relates to medical imaging systems, and more particularly to systems and methods for detecting and presenting textural information from medical images.

BACKGROUND OF THE INVENTION

Intraluminal, intracavity, intravascular, and intracardiac treatments and diagnosis of medical conditions utilizing minimally invasive procedures are effective tools in many areas of medical practice. These procedures are typically performed using imaging and treatment catheters that are inserted percutaneously into the body and into an accessible vessel of the vascular system at a site remote from the vessel or organ to be diagnosed and/or treated, such as the femoral artery. The catheter is then advanced through the vessels of the vascular system to the region of the body to be treated. The catheter may be equipped with an imaging device, typically an ultrasound imaging device, which is used to locate and diagnose a diseased portion of the body, such as a stenosed region of an artery. For example, U.S. Pat. No. 5,368,035, issued to Hamm et al., the disclosure of which is incorporated herein by reference, describes a catheter having an intravascular ultrasound imaging transducer.

FIG. 1a shows an example of an imaging transducer assembly 1 known in the art. The imaging transducer 1 is typically within the lumen 10 of a guidewire (partially shown), having an outer tubular wall member 5. To obtain an image of a blood vessel, the imaging transducer assembly 1 may be inserted into the vessel. The transducer assembly 1 may then rotate while simultaneously emitting energy pulses, e.g., ultrasound waves, at portions of the vessel from within the vessel and receiving echo or reflected signals.

Turning to FIG. 1b, it is known in the art that an imaging console 20 having a display screen, a processor and associated graphics hardware (not shown) may be coupled with the imaging transducer assembly 1 to form a medical imaging system 30. The imaging console 20 processes the received echo signals from the imaging transducer assembly 1 and forms images of the area being imaged. To form the images, the imaging console 20 draws multiple lines, known as "radial lines", (not shown) on the display screen that each correspond to an angular position of the transducer assembly 1. The processor of the imaging console 20 assigns brightness values to pixels of the lines based on magnitude levels of the echo signals received from the transducer assembly 1 at the angular positions corresponding to the lines. A drawing that includes a large number of these radial lines results in an image such as an intravascular ultrasound (IVUS) image (not shown). Such an image may show, among other things, the texture of the area being imaged, such as the smoothness or the roughness of the surface of the area being imaged.

An example of an image 70 having a large range of magnitudes and a number of texturally distinct regions 80 is shown in FIG. 1c. Texture and the correct discrimination of the underlying surface are important in medical imaging. Such information is helpful to radiologists and other clinicians who seek to diagnose pathology. It is often the case in medical imagery that an abnormality is detectable only as a subtle variation in texture. Accordingly, an improved system and method for detecting and presenting such textural information would be desirable.

SUMMARY OF THE INVENTION

The invention is directed to systems and methods for detecting and presenting textural information from medical images. In one example embodiment, a medical imaging system includes an imaging transducer assembly configured to emit one or more energy pulses and receive one or more echo signals, and a console, coupled to the imaging transducer assembly, configured to receive the one or more echo signals, generate an uncompressed image based on the one or more echo signals, generate a compressed image based on the uncompressed image, generate a color overlay based on the uncompressed image, and apply the color overlay to the compressed image. In another example embodiment, the compressed image may be a log compressed image.

In yet another example embodiment, a medical imaging system includes an imaging transducer assembly configured to emit one or more energy pulses and receive one or more echo signals, each having a magnitude level, and a console, coupled to the imaging transducer assembly, configured to receive the one or more echo signals, generate an image based on the one or more echo signals, and add auditory information to the image based on the magnitude levels of the image.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the inventions are obtained, a more particular description of the embodiments briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION OF THE PREFERRED EMBODIMENTS

Figure 1A:
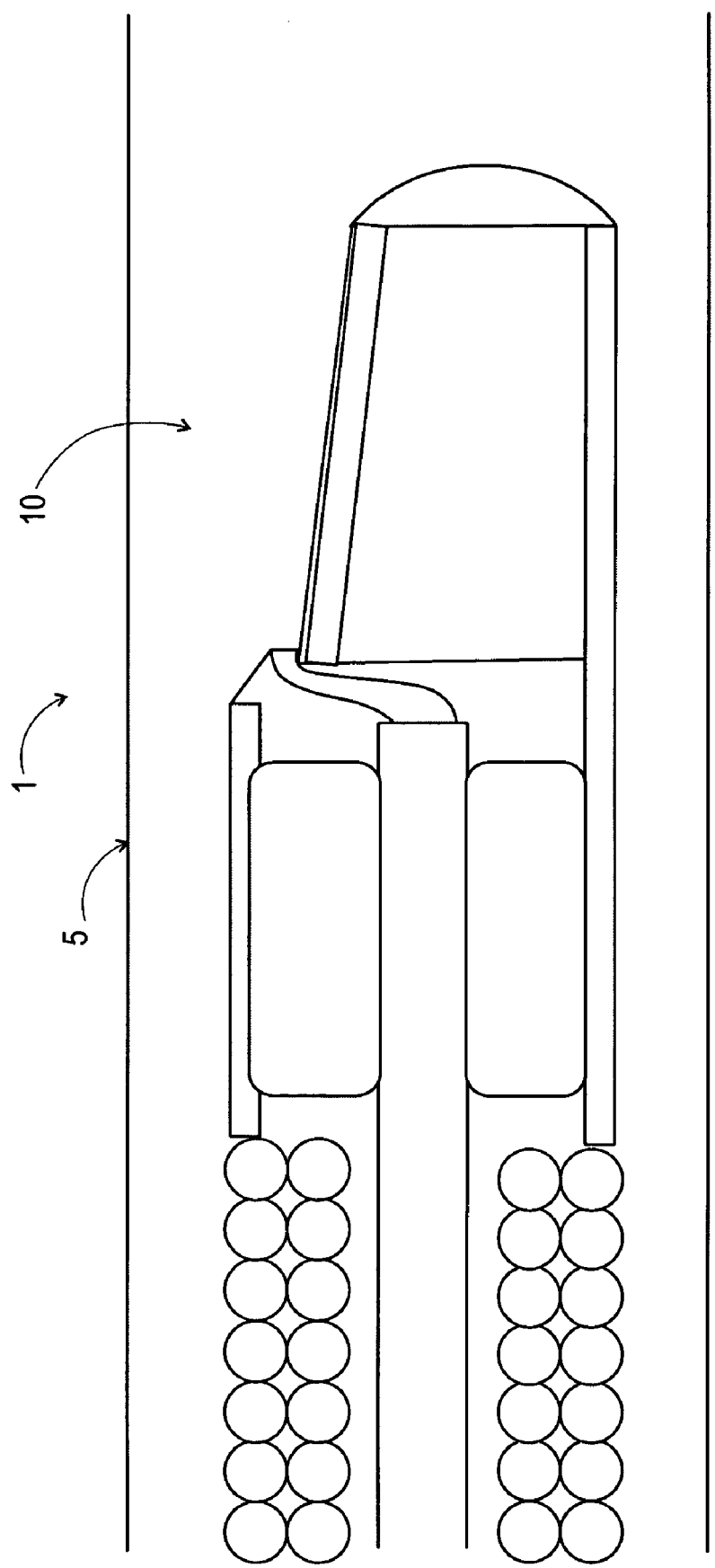
FIG. 1a is a cross-sectional side view of an imaging transducer assembly known in the art.
Figure 1B:
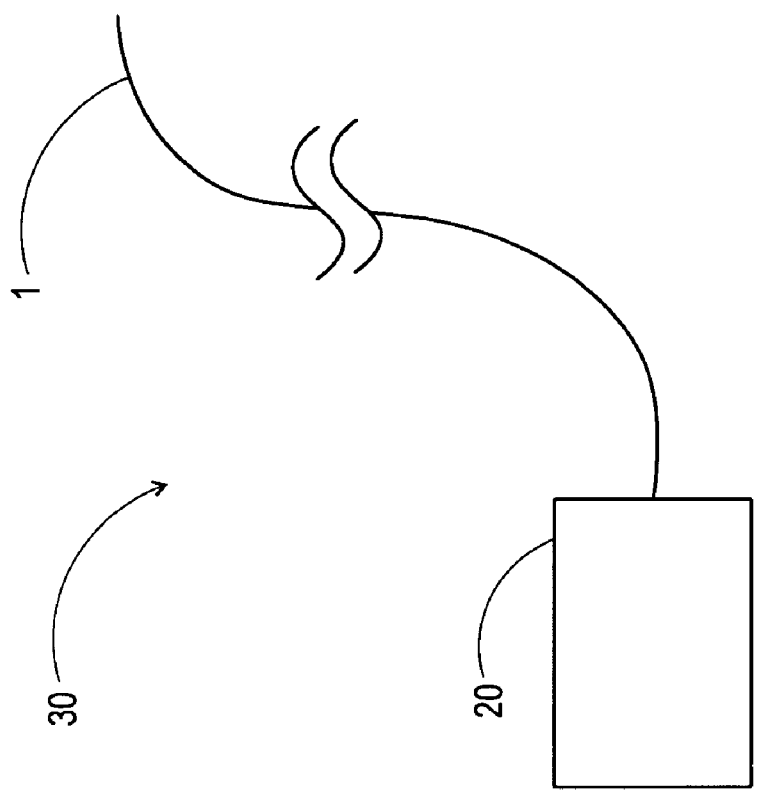
FIG. 1b is a block diagram of a medical imaging system known in the art.

Turning to FIG. 1b, a typical imaging system 30 may include an imaging transducer assembly 1 and coupled to the imaging transducer assembly 1, an imaging console 20 having a display screen, a processor and associated graphics hardware (not shown). To form an image of body tissue by an intravascular ultrasound system (IVUS), the imaging transducer assembly 1 emits energy pulses, such as ultrasound pulses, and receives echo signals from those pulses after they are reflected by body tissue (tissue, fat, bone, vessel, plaque, etc., or other object). If desired, the imaging transducer may emit energy pulses while simultaneously rotating about a central axis or translate longitudinally along the central axis. The imaging console 20 receives the echo signals from the imaging transducer assembly 1 and draws lines on the display screen that each correspond to an angular position of the transducer assembly 1 as the transducer assembly 1 rotates. The processor of the imaging console 20 assigns brightness values to pixels of the lines based on the magnitude levels of echo signals received from the transducer assembly 1 at the corresponding angular positions. A drawing that includes a large number of these lines ("radial lines") results in an image, such as an IVUS image (not shown). Such an image may provide textural information about the area being imaged, such as the appearance of blood speckle.

The echo signals received are typically classified by records, or vectors, corresponding to a particular angular position. Each record, or vector, for a particular angular position contains oscillations covering a large range of magnitudes. The largest of the oscillations might be several tens of thousands stronger than the smallest of oscillations. However, a display device, such as a monitor (CRT, liquid crystal display, plasma, etc.), typically only recognizes a limited number (e.g., 256) of gray levels. Thus, the ability to differentiate between texturally distinct regions may be limited, and some of the regions may be too dim to be seen clearly in such a device, and may be hard to distinguish from adjacent regions.

Figure 1C:
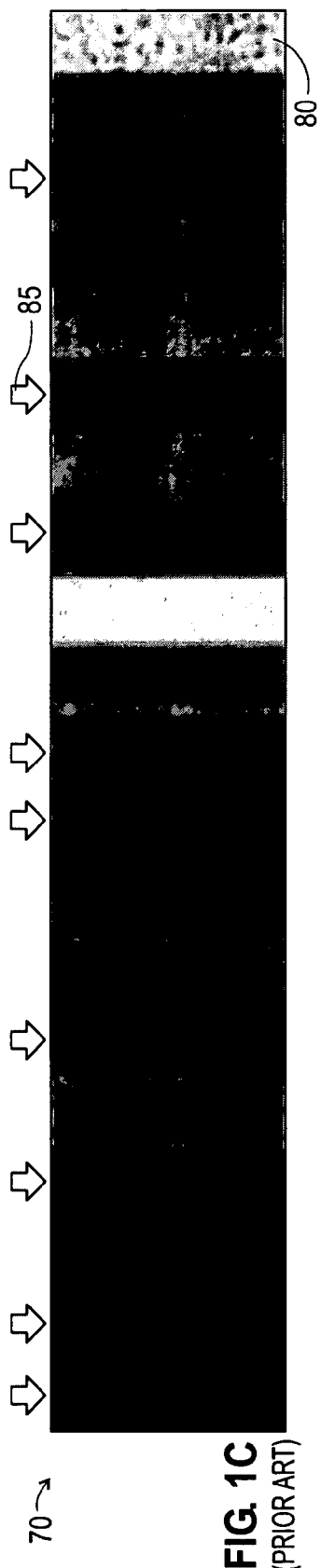
FIG. 1c is an example of an image showing different magnitudes and textures.

An example of an image 70, which may be an image of received echo signals, containing a large range of magnitudes and a number of texturally distinct regions 80 is shown in FIG. 1c. The very dim textural regions are marked by arrows 85. One approach to effectively translate the range of magnitudes of the image is to use a logarithmic scale. The result is that the large range of magnitudes is compressed so that all the portions of the image may be represented on a gray scale having only a limited number of levels. The process of compressing the image using a logarithmic scale is known as a "log compression." An example of a log compressed image 100 is shown on FIG. 1d. A disadvantage to applying log compression is that some of the potentially useful textural information present in the original echo signal may be lost or altered. For example, in FIG. 1d, some of the lines that displayed more texturally distinct characteristics in FIG. 1c now have lost their distinct appearances to the human eye, as marked by arrows 110. Thus, it would be useful to have an approach to enhance the textural information in such an image 100 so as to be readily apparent to a human observer, such as a physician, physician's assistant, or nurse.

Figure 1D:
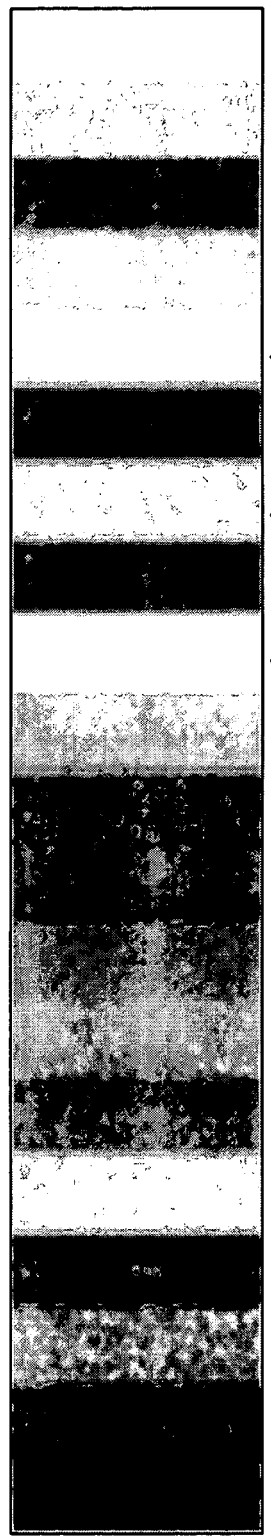
FIG. 1d is an example of a log compressed image based on the image from FIG. 1c.
Figure 2:
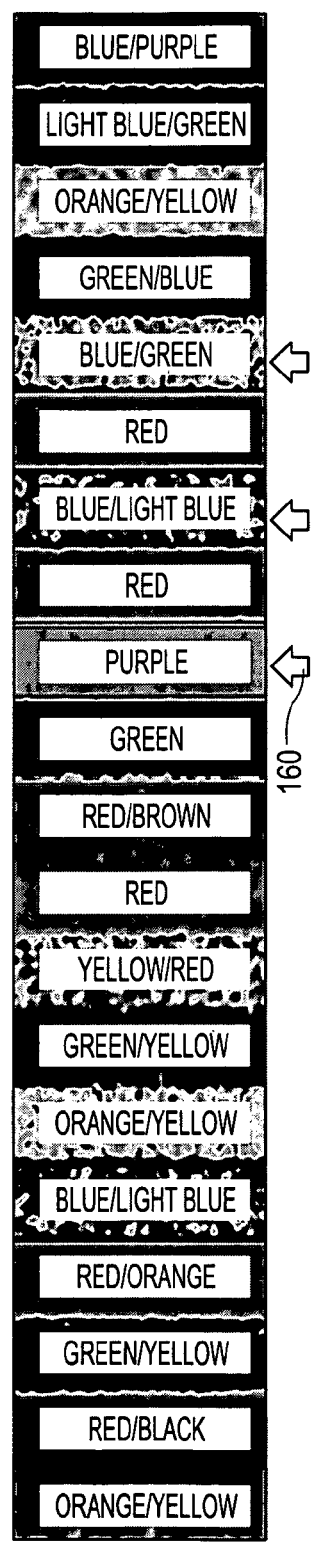
FIG. 2 is an example of an image generated in accordance with a preferred example embodiment of the invention.

In one approach, an overlay that uses color, as opposed to a gray scale, may be generated based on the original uncompressed image. A distinct color may be assigned to a magnitude level, e.g., magnitude level of an echo signal, for a pre-determined number of levels. The color overlay may then be generated based on the original uncompressed image and the color assignments and then applied on the log compressed image 100 shown in FIG. 1c. An example result of an image 150 with such a color overlay is shown in FIG. 2. The arrows 110 of the image 100 in FIG. 1d mark texturally distinct regions 80 of which the textural distinctness is not readily apparent. By applying a color overlay, as shown in FIG. 2, the arrows 160 show that those regions marked by arrows 110 of the image 100 in FIG. 1d are much more distinct to the human eye, i.e., one shows as blue/green, another as blue/light blue, and the last one as purple.

Figure 3:
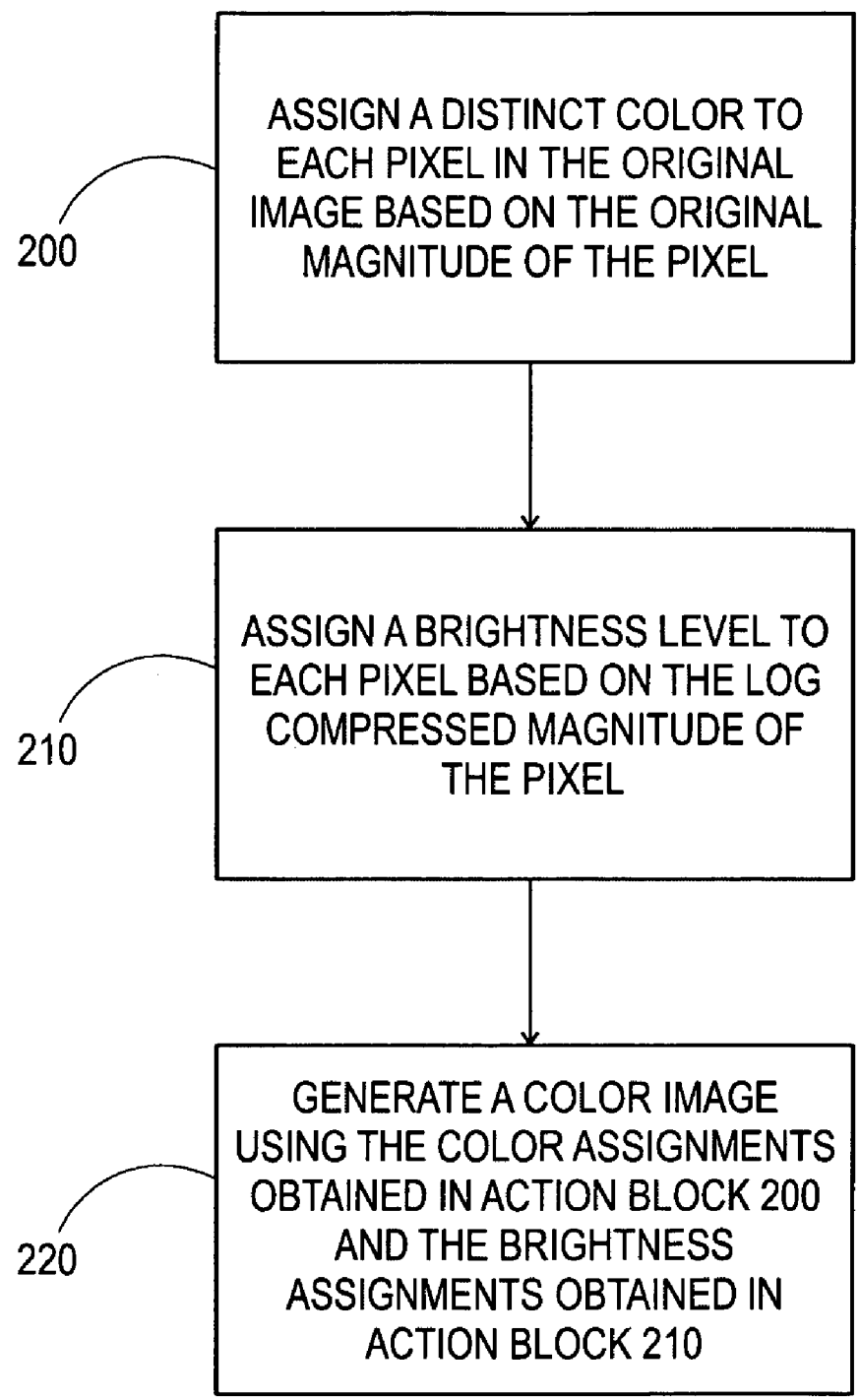
FIG. 3 is a diagram of the operation of a preferred example embodiment of the invention.

In one embodiment, a system having a processor, a display, and hardware and software to process graphics (not shown) may perform the method illustrated in FIG. 3. As one of ordinary skill in the art may appreciate, the system may be configured to receive echo signals from an imaging transducer assembly and then perform the following functions. First, the system may assign a distinct color to each pixel in the original image based on the original magnitude of the pixel (action block 200). Next, the system may assign a brightness level to each pixel based on the log compressed magnitude of the pixel (action block 210). Next, the system may generate a colorized image using the color assignments obtained in action block 200 and the brightness assignments obtained in action block 210 (action block 220). The colorized image may then be saved on a computer storage medium for further analysis.

In another embodiment, the appearance of the image may be controlled by a user-friendly interface, such as a spring-loaded knob, keyboard, mouse, and/or a software application having a graphical user interface. If a particular area of interest is being imaged, a user may adjust, e.g., turn the knob, to control the amount of colorization for closer or further inspection of textural information for the particular area of interest. If desired, the operator may be permitted through the user interface to change the colors that have been assigned to the magnitude levels. Such customization of color assignment may help make distinctions in levels more perceptible to the human operator, or a partially color blind human operator.

In yet another embodiment, instead of assigning different colors to the different magnitude levels for the echo signals, different sounds, e.g., different tones or different patterns, may be assigned to the different magnitude levels, allowing for textural information to be presented as auditory information. Further, instead of, or in addition to, assigning sounds at such a granular level, sounds may be assigned based on different combinations of magnitude levels within an image.

In still another embodiment, in addition to assigning different colors to the different magnitude levels for the echo signals, different sounds also may be assigned to the different magnitude levels, allowing for textural information to be presented as auditory and visual information. Further, instead of, or in addition to, assigning sounds at such a granular level, sounds may be assigned based on different combinations of magnitude levels within an image.

Another modification includes a mouse or pointing device. Thus, for example, when the operator uses the mouse or pointing device to point to a certain line of an image, the system will output the audible sound assigned to that magnitude level through a speaker. By moving the pointer to different lines, differences in the magnitude level may be audibly perceived by the human operator. Therefore, if the color or grey scale overlay does not permit the human operator to perceive readily whether one line has a different magnitude, and how much of a difference, the human operator can use the auditory assignments to listen to the tone for the lines at issue.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention can be performed using different or additional process actions, or a different combination or ordering of process actions. For example, this invention is particularly suited for applications involving medical imaging devices, but can be used on any design involving imaging devices in general. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is:

1. A medical imaging system comprising:
    an imaging transducer assembly configured to emit one or more energy pulses and receive one or more echo signals, each having a magnitude level;
    a console coupled to the imaging transducer assembly and configured to receive the one or more echo signals, generate one or more images based on the one or more echo signals, compress the one or more images into one or more compressed images, and add auditory information to the one or more compressed images based on the magnitude levels of the one or more images before compression.

2. The medical imaging system of claim 1, wherein the compression of the one or more images comprises log compression.

3. The medical imaging system of claim 2, wherein the console is configured to add auditory information to the one or more log compressed images based on one or more combinations of magnitude levels of the one or more images before compression.

4. The medical imaging system of claim 1, wherein the imaging transducer assembly has an axis and is configured to rotate on its axis, and wherein the imaging transducer assembly emits energy pulses and receives one or more echo signals while rotating on its axis.

5. The medical imaging system of claim 4, further comprising a control that permits the operator to change the auditory signal assigned to a magnitude level.

6. The medical imaging system of claim 1, wherein the imaging transducer assembly is an ultrasound transducer assembly.

7. The medical imaging system of claim 1, wherein the auditory information is added based on one or more combinations of magnitude levels of the one or more images before compression.

8. The medical imaging system of claim 1, further comprising a control that permits the operator to change the auditory signal assigned to a magnitude level.

9. The medical imaging system of claim 1, wherein the magnitude levels are time varying.

10. A method for generating a medical image comprising the steps of:
    assigning an auditory signal to each of a plurality of magnitude levels;
    receiving one or more echo signals reflected from body tissue, each having a magnitude level;
    generating an image having one or more lines, wherein each line corresponds to one of the one or more echo signals;
    compressing the image into a compressed image; and
    adding one or more auditory signals corresponding to the one or more lines of the compressed image based on the magnitude levels of the one or more lines of the image before compression.

11. The method of claim 10, wherein the one or more lines are one or more radial lines.

12. The method of claim 10, wherein the one or more lines are one or more vectors.

13. The method of claim 10, wherein the echo signals are ultrasound echo signals.

14. The method of claim 10, wherein compressing the image comprises log compressing the image.

15. The method of claim 10 further comprising changing an auditory signal assigned to a magnitude level.

16. A method for evaluating an ultrasound image comprising the steps of:
    reviewing a compressed ultrasound image having one or more lines, each line corresponding to an echo signal reflected from body tissue;
    selecting a portion of the compressed ultrasound image; and
    generating an auditory signal corresponding to the selected portion of the compressed ultrasound image, wherein the auditory signal is based on a magnitude level of the selected portion of the ultrasound image before compression of the ultrasound image, and wherein the audio signal is added to the ultrasound image after compression of the ultrasound image.

17. The method of claim 16, wherein the selected portion of the compressed image is log compressed.

\* \* \* \* \*

UNITED STATES PATENT AND TRADEMARK OFFICE
CERTIFICATE OF CORRECTION

PATENT NO. : 7,578,790 B2
APPLICATION NO. : 10/896104
DATED : August 25, 2009
INVENTOR(S) : Shashidhar Sathyanarayana It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 526 days.

Signed and Sealed this

Seventh Day of September, 2010

David J. Kappos
*Director of the United States Patent and Trademark Office*